United States Patent [19]

DeWitt

[11] Patent Number: 4,771,772

[45] Date of Patent: Sep. 20, 1988

[54] ROBOTIC IMPLANTABLE MEDICAL DEVICE AND/OR COMPONENT RESTORATION SYSTEM

[75] Inventor: James L. DeWitt, Park City, Utah

[73] Assignee: Medtronic, Inc., Minneapolis, Minn.

[21] Appl. No.: 923,487

[22] Filed: Oct. 27, 1986

Related U.S. Application Data

[60] Division of Ser. No. 684,841, Dec. 21, 1984, Pat. No. 4,628,928, which is a continuation of Ser. No. 406,197, Aug. 9, 1982, abandoned.

[51] Int. Cl.⁴ .............................................. A61B 17/00
[52] U.S. Cl. .................................. 128/303 R; 128/675; 604/267; 604/266
[58] Field of Search ................. 128/303 R, 675, 673; 604/151, 167, 266–269, 250; 73/861.12, 432 B

[56] References Cited

U.S. PATENT DOCUMENTS

| | | | |
|---|---|---|---|
| 2,328,199 | 8/1943 | Day | 604/267 |
| 2,804,075 | 8/1957 | Borden | 604/269 |
| 2,844,351 | 7/1958 | Smith | 604/250 |
| 3,409,031 | 11/1968 | Benbow et al. | |
| 3,453,546 | 7/1969 | Fryer | |
| 3,479,873 | 11/1969 | Hermanns | |
| 3,542,031 | 11/1970 | Taylor | 694/269 |
| 3,581,733 | 6/1971 | Grandjean | |
| 3,709,211 | 1/1973 | Hawkins | 604/267 |
| 3,798,474 | 3/1974 | Cassand et al. | |
| 3,813,938 | 6/1974 | Grosch et al. | |
| 3,923,060 | 12/1975 | Ellinwood, Jr. | |
| 3,958,573 | 5/1976 | Wiley | 604/267 |
| 4,003,379 | 1/1977 | Ellinwood, Jr. | |
| 4,013,074 | 3/1977 | Siposs | |
| 4,125,019 | 11/1978 | Cushing | |
| 4,146,029 | 3/1979 | Ellinwood, Jr. | |
| 4,183,010 | 1/1980 | Miller | |
| 4,191,181 | 3/1980 | Franetzke et al. | |
| 4,228,802 | 10/1980 | Trott | 604/267 |
| 4,267,835 | 5/1981 | Barger et al. | 604/250 |
| 4,278,083 | 7/1981 | Young et al. | 604/250 |
| 4,316,115 | 2/1982 | Wilson et al. | |
| 4,341,224 | 7/1982 | Stevens | |
| 4,359,054 | 11/1982 | Leist et al. | |
| 4,360,019 | 11/1982 | Portner et al. | |
| 4,375,170 | 3/1983 | Sperry, III et al. | |
| 4,407,296 | 10/1983 | Anderson | |
| 4,424,833 | 1/1984 | Spector et al. | |
| 4,444,198 | 4/1984 | Petre | |
| 4,458,877 | 7/1984 | Holmes | 604/250 |
| 4,509,947 | 4/1985 | Lattin | |
| 4,540,411 | 9/1985 | Bodicky | 604/250 |
| 4,550,748 | 11/1985 | Nunez | 604/250 |
| 4,628,928 | 12/1986 | Lowell | 128/303 R |

FOREIGN PATENT DOCUMENTS

| | | |
|---|---|---|
| 2420853 | 11/1979 | France |
| 29753 | 3/1978 | Japan |
| 602195 | 4/1978 | U.S.S.R. |

Primary Examiner—C. Fred Rosenbaum
Assistant Examiner—Gene B. Kartchner
Attorney, Agent, or Firm—Mallinckrodt & Mallinckrodt

[57] ABSTRACT

In combination with a device adapted for at least partial implantation in a living body to perform a function with respect to that body such as introducing a material into the body, relieving the body of a material, monitoring a condition within the body, or introducing electrical stimulus into the body, servicing apparatus is provided in association with the device for maintaining the device in effective operating condition. The device and servicing apparatus may be arranged in a single housing such that a portion of the device extends from the housing into operable position in the body, in separate but operably connected housings, or the servicing apparatus may be split between the device and a separate housing. The actual servicing of the device may be done within a service housing where the portion of the device to be serviced is drawn into the service housing and mechanically or chemically serviced, the servicing instrumentality may be moved from a service housing to the device to be serviced when servicing is necessary, or a portion of the servicing instrumentality may be built in or permanently positioned with respect to the device and operated by the remainder of the servicing apparatus located in a common housing with the device or in a separate housing.

Circuitry is preferably provided to initiate and control the servicing operation.

28 Claims, 6 Drawing Sheets

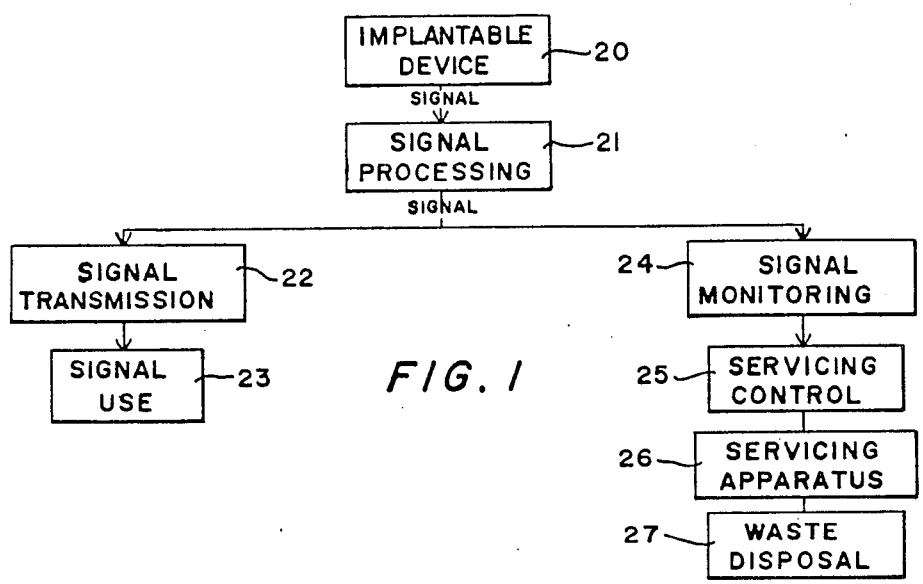
FIG. 1
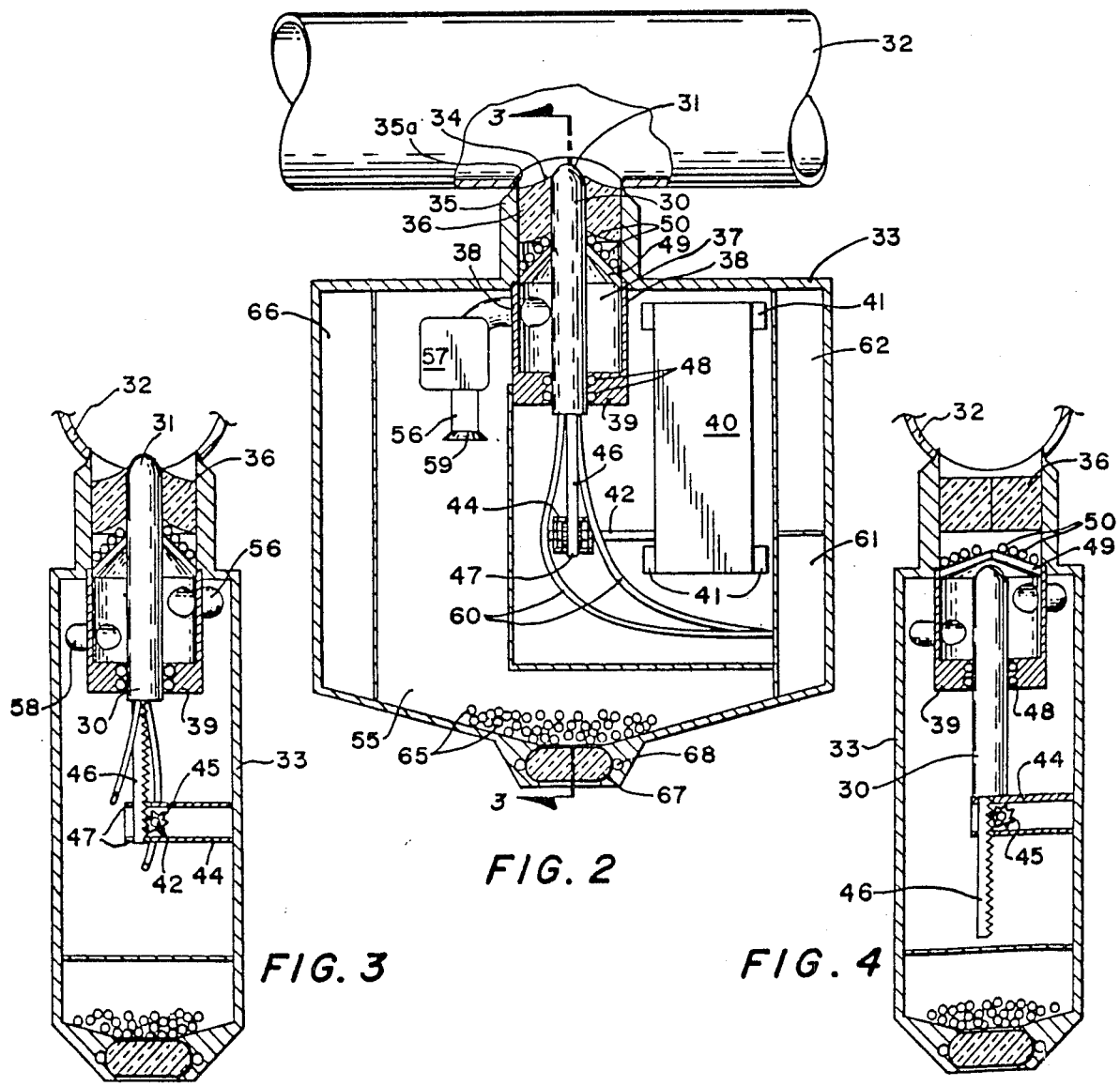
FIG. 2
FIG. 3
FIG. 4

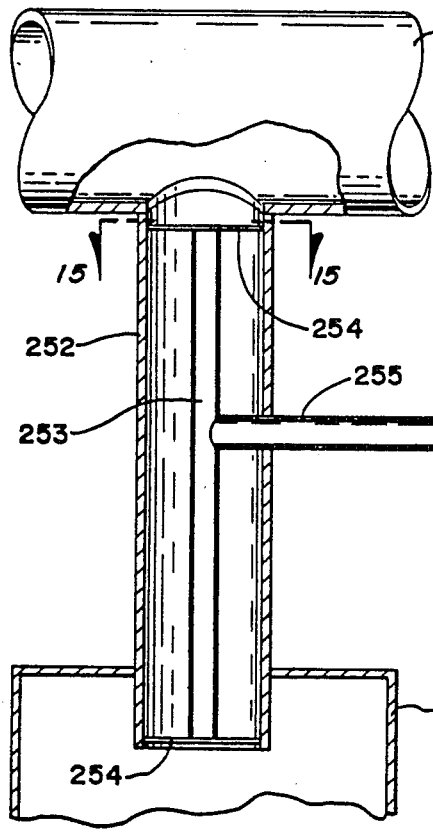
FIG. 14
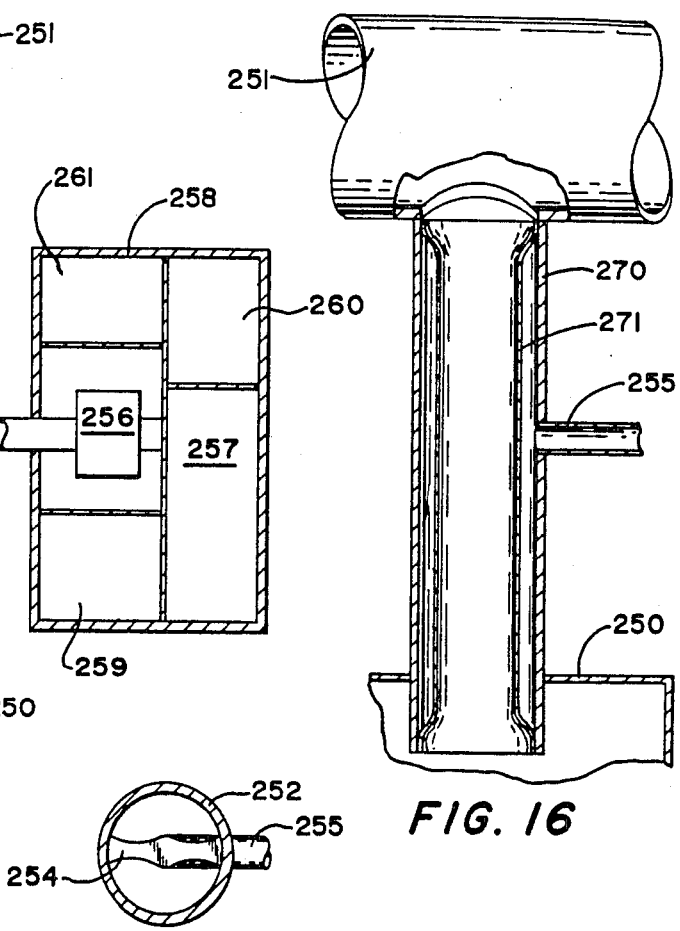
FIG. 16
FIG. 15
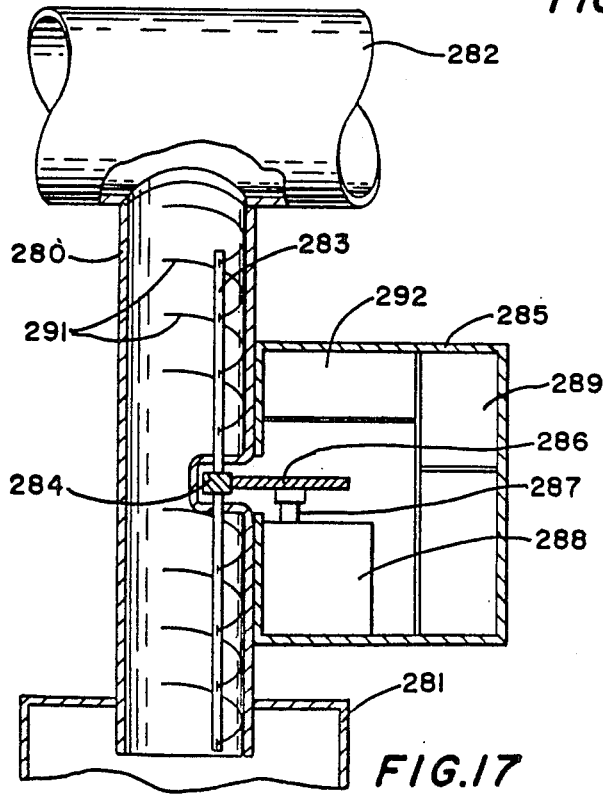
FIG. 17
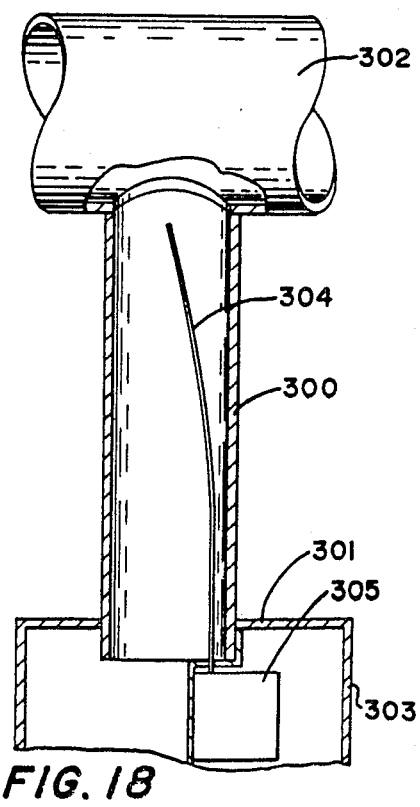
FIG. 18

ROBOTIC IMPLANTABLE MEDICAL DEVICE AND/OR COMPONENT RESTORATION SYSTEM

This is a division of application Ser. No. 684,841, filed Dec. 21, 1984, U.S. Pat. No. 4,628,928, which was a continuation of application Ser. No. 406,197, filed Aug. 9, 1982 now abandoned.

BACKGROUND OF THE INVENTION

1. Field

The invention is concerned with devices for implantation or partial implantation in living human or animal bodies.

2. State of the Art

There are currently many devices that have been developed for full or partial implantation into a living body. These include heart pacemakers, pumps for administering medication, electrodes, sensors of various kinds, and attendant electrical leads, catheters, and tubing, for continuously monitoring certain body conditions.

These devices generally have limited life in the adverse biological environment of the body and need to be replaced periodically. However, each time such a device is replaced, it requires major surgery with the accompanying risks.

One reason that replacement of such devices is periodically required is the tendency for materials to build up on or in critical portions of the device, thereby seriously interfering with proper and effective operation. The build-up may be of natural body materials or of materials discharged by the device or it may be a combination or result from an interaction of these. Thus, when a device is implanted, because of the body's tendency to reject or isolate foreign material, body material will start to build up on and around the device.

If a sensor, for example, is placed in the blood stream, the blood will tend to coagulate and build up on the sensing surface. After a period of time, this build-up of material can severely interfere with the operation of the sensor, making replacement necessary. The same problem occurs in other parts of the body with build-up of cells, tissue, and various other materials, such as sheetings of protein. Also, where a membrane or other surface is used for passing only selected molecules, it may become poisoned, i.e., blocked or clogged, by other molecules. Again, with devices other than sensors, similar problems can arise. Such devices are rendered ineffective or inoperable after a period of time by the build-up thereon of foreign materials.

With devices which discharge a material during operation, such as pumps by which medication is continuously or periodically supplied to the blood stream or to other parts of the body through catheters or otherwise, the catheter or other passages often become blocked by precipitation of the material being pumped, by blood clots, or by other build-up, thereby rendering the entire pumping device ineffective or inoperable. For example, with pumps for pumping insulin or other proteins, the material being pumped into the body has a tendency to precipitate in the catheter, thereby clogging it. Also, materials from the device itself, such as gases or other chemicals released over periods of time from materials used in construction of the device, may build up or interact with body materials to thereby interfere with the device's operations. Again, under these conditions replacement of the device is necessary. With devices such as heart pacemakers, neuro-stimulators, or electronic bridging circuits where electrical leads extend from the device to body parts or between body parts, the leads themselves, particularly where they attach to body parts, may be subject to material growth or build-up to the point where conduction between the lead and body part may be seriously affected.

A second reason necessitating replacement of some devices, such as various sensors, is that the devices themselves will degrade or wear out with time, so that operation is no longer satisfactory.

Presently, there is no known way to restore, rehabilitate, clean, or otherwise service a device, whose operation has become seriously degraded, ineffective, inefficient, or has ceased completely, while such device remains in the body.

One of the current pressing needs for appropriate insulin administration is the development of a long term, implantable, glucose sensor. Such a glucose sensor is urgently needed to provide an adequate, closed loop, insulin administration system, as, for example, one in which an implantable insulin pump is used so that insulin administration will closely follow normal body routine. There are currently no glucose sensors available which will maintain sensing ability in vivo for more than a few hours or days. Since replacement of such a sensor on a daily basis is entirely impractical, implantable insulin pumps have had only limited use. However, if a known type of glucose sensor could be restored within the body, extensive use of implantable insulin pumps would become a reality.

SUMMARY OF THE INVENTION

According to the invention, devices wholly or partially implanted into the adverse biological environment of a living body are serviced by servicing means associated with the device, while remaining in body-compatible sterile condition. In this way, a device is maintained in operating condition within the body for much longer periods of time than would otherwise be the case.

The term "device" as here used refers to any instrumentality currently known or which may be developed in the future for implantation wholly or partially, into a living body for any purpose. Examples are sensors, medication or drug pumps, catheters, tubing, electrodes, electrical leads.

The servicing means will generally be connected with the device in such a way that it also will be wholly or partially implanted in the living body, either as a single unit including both the device and the servicing means in a single housing, a separate unit connected to the device, or as multiple but interconnected units. Where the device to be serviced is only partially implanted, the servicing means connected thereto could be located completely outside the body, but within a service housing mounted on the body, such as by being supportively attached to the skin over or about the device, by being supportively attached to the device itself where it projects from the skin, or by otherwise being supportively mounted outside the body as on a belt or harness. While it is contemplated that the service housing will generally be permanently connected to the device so as to maintain a sterile connection, it is possible that the service housing and the device may be disconnectable and the service housing connected to the device in a sterile manner when servicing is necessary. Similarly, a portion of the service housing may be permanently connected to the device while another portion of such housing may be disconnectable to be attached when servicing is desired, or as otherwise necessary. In such case, the portion to be attached may be the actual servicing means where attachment would be made so as to be sterile, or the portion to be attached could merely be a power supply or similar item where attachment can be made without regard to sterility.

The device and servicing means may be arranged so that the device itself, or a portion of it is actually drawn into a service housing to be serviced. In such instance, the physical connection between the housing and device may take various forms such as the housing and device being connected and forming a single unit so that the device extends through an opening in the housing into its operable position. With such arrangement, means are provided to withdraw the device through the opening into the housing which provides a controlled, sterile environment and to close such opening to the body thereafter. The servicing means, such as cleaning and restoring instrumentalities, are located within the controlled environment of the housing to restore the device to its operable condition, and means are provided to again extend the device into its operable position within the body after servicing is completed.

The device and servicing means may be arranged so that the servicing means is extended from a service housing to bring it into juxtaposition with the device for servicing. An example of this type of arrangement is in connection with a catheter where the housing may be connected to the catheter by a Y-type connection and an obturator in the housing is extended into the catheter to an area of blockage to dislodge or break up the blockage, such as a clot, to thereby clean the catheter.

The device and servicing means may be arranged so that a portion of the servicing means is built into and included as a portion of the device to be serviced or is permanently positioned with respect to the device, and that portion of the servicing means is operated from the remaining portion of the servicing means located in a service housing. An example of this type of arrangement is in connection with a catheter having expandable internal walls or an internal expandable tube member, and the service housing is connected to the catheter by tubing so that a pressurized fluid from the housing is connected to expand the internal walls of the catheter inwardly or to expand the internal tube member outwardly to fill up the catheter lumen and thereby dislodge or break up any blockage. A further example of this type of arrangement is in connection with a catheter having a wire extending through the lumen and the service housing is mechanically connected to the catheter so that a motor in the housing drives the wire to thereby cause it to rotate, snake, or otherwise move in the catheter lumen to break up or dislodge blockage and clean the catheter.

The device may be serviced on a periodic basis or only when necessary as indicated by poor performance of the device.

Cleaning and restoring may take several forms, such as a solution soak, a mechanical cleaning, provision for replacement of the active portion of the device, extension of an obturator through the device, the forcing of pressurized fluid into or through the device, the movement of mechanisms within the device, or the modification of internal portions or characteristics of the device.

In some cases, the debris cleaned or otherwise removed from a device may be stored within the housing either in a free state as it is removed from the device, or as adhered to some surface or material within the housing. Such surface may be fluid reservoir walls which, in some circumstances, may be specially formed to provide a maximum surface area. In other instances, it may be necessary to dispose of the material which has been cleaned from the device, and this also may be done in a variety of ways such as by inserting a syringe needle through the skin and into a reservoir in the service housing and withdrawing spent fluid and replacing it with fresh fluid, replacing or regenerating an ion exchange material in the service housing, expelling the debris from the housing through a catheter or other connection to outside the body, or the debris may be fed into the body to be disposed of by body functions.

The invention also involves the method of maintaining an at least partially body-implanted device viable for its intended purpose by operably connecting the device and a service housing provided with means for servicing the device while maintaining it in a body compatible sterile condition, bringing the device and the servicing means into juxtaposition for servicing the device, and controlling the servicing of the device.

THE DRAWINGS

In the accompanying drawings which represent several embodiments constituting the best modes presently contemplated for carrying out the invention:

FIG. 1 is a block diagram showing a specific system of the invention;

FIG. 2, a vertical section through the service housing of one embodiment of the invention in which the device to be serviced is drawn into the housing for servicing and the servicing instrumentality is a fluid;

FIG. 3, a vertical section taken on the line 3—3 of FIG. 2;

FIG. 4, a view similar to FIG. 3, but showing the sensor in withdrawn position;

FIG. 5, a view similar to FIG. 2, but showing a mechanical servicing instrumentality;

FIG. 6, a fragmentary view showing the servicing chamber portion of FIG. 5, drawn to a larger scale with the sensor tip in the servicing chamber;

FIG. 7, a view similar to FIG. 2, but showing a servicing instrumentality which replaces a portion of a sensor being serviced;

FIG. 8, a fragmentary horizontal section taken on the line 8—8 of FIG. 7,

FIG. 9, an exploded view of the sensor of FIG. 7 showing how the sensor tip fits into the sensor base;

FIG. 10, a fragmentary view of a portion of the service chamber as shown in FIG. 7, with the sensor in retracted position;

FIG. 11, a fragmentary view in vertical section taken on the line 11—11 of FIG. 10 to show a portion of the service chamber of FIG. 7 with a sensor tip tray in a rotated position and between stops;

FIG. 12, a vertical section through the service housing and associated catheter to be serviced of an embodiment of the invention in which the servicing instrumentality is an obturator extended from the service housing into the catheter to be serviced;

FIG. 13, a vertical section through the service housing and an associated catheter to be serviced in an embodiment of the invention in which the servicing instrumentality is a fluid which is pumped from the service housing into the catheter to be serviced;

FIG. 14, a vertical section through the service housing and associated catheter to be serviced in an embodiment of the invention in which a portion of the servicing instrumentality is positioned within the catheter to be serviced and is operated by pressurized fluid from the service housing;

FIG. 15, a horizontal section taken on the line 15—15 of FIG. 14;

FIG. 16, a vertical section similar to that of FIG. 14 taken through another embodiment of a catheter to be serviced, in which a portion of the servicing instrumentality is built into the catheter and is adapted to be operated by pressure fluid from the service housing of FIG. 14;

FIG. 17, a similar vertical section taken through the service housing and associated catheter of another embodiment of the invention in which a portion of the servicing instrumentality is built into the catheter and is operated by a motor in the service housing;

FIG. 18, a similar vertical section taken through still another embodiment of the invention wherein the implanted device includes a housing and a catheter to be serviced, and wherein the service housing is located within the housing of the device;

FIG. 19, a view in side elevation of an embodiment of the invention wherein a catheter has a portion of the servicing instrumentality built in for use with the service housing of FIG. 17, only a fragmentary portion of such housing being shown;

FIG. 20, a vertical section similar to those of FIGS. 14 and 16–18 taken through an embodiment of service housing and associated catheter to be serviced, wherein the catheter and therein positioned portion of the servicing instrumentality are shown in elevation;

FIG. 21, a similar vertical section through a somewhat different embodiment of the invention; and FIG. 22, a vertical section through the catheter portion of a similar embodiment using a somewhat different type of servicing instrumentality from the service housing shown in FIG. 21.

DETAILED DESCRIPTION OF THE ILLUSTRATED EMBODIMENTS

Figure 5:
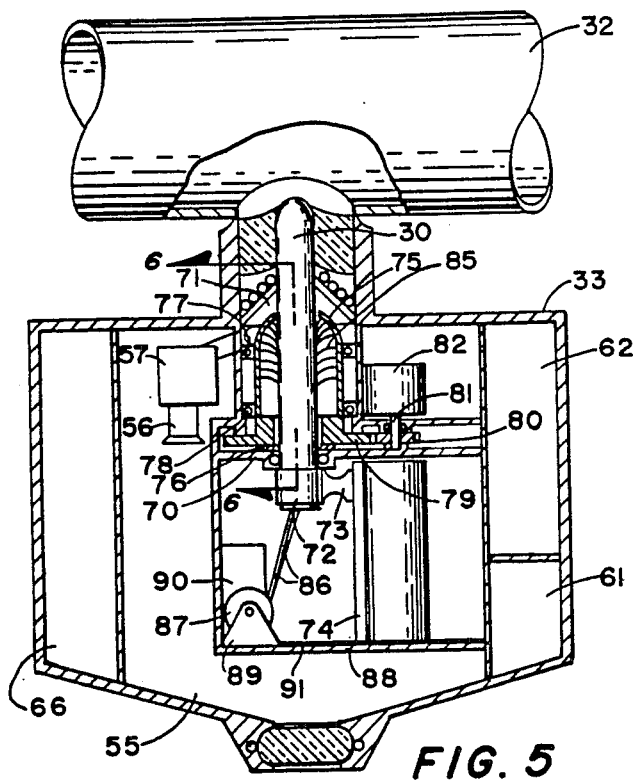

FIG. 1 shows a general block diagram of one embodiment of the inventive combination. The implantable device 20 may be one of a wide variety of such devices, such as for introducing a material into the body, relieving the body of a material, monitoring a condition within the body, or introducing electrical stimulus into the body. Examples of such devices may be various types of sensors, solid state receptors, or transducers, e.g. pressure sensors, glucose sensors, pH sensors, specific ion sensors, enzyme sensors, specific molecule concentration sensors, gas sensors, fuel cells, CHEMFETs, ISFETs, or any device sensitive to specific conditions or environments; heart pacemakers; neurostimulators; electrical leads or catheters connecting body parts; electrodes; drug pumps for the supply of drugs or other medication to target sites through catheters or other passageways; or any other type of device which may be implanted for any reason in the body together with attendant electrical leads or catheters.

Many implantable devices, particularly sensors, are implanted in the body to produce electrical signals indicative of a sensed condition and such signals are then monitored inside or outside the body or used to control operation of some other device, such as a drug pump or pacemaker. Further, with devices other than sensors whose purpose is not to produce electrical signals but is to perform some other function, such as drug administration by means of a drug pump, a sensor of some type may be included in the device so that the device's operation can be monitored.

Thus, electrical signals from the device are processed by signal processing circuitry 21 to put them into useable form and are transmitted by signal transmission circuitry 22 to the place of use, indicated generally by block 23. If the signals are to be used to control the operation of a drug pump or pacemaker, the signal transmission circuitry will probably merely be wires directly connecting the signal processing circuitry to the control circuitry of the pump or pacemaker, such control circuitry being represented by block 23 labeled signal use. If the signals are to be monitored outside the body, the signal transmission circuitry may take the form of well known telemetry circuits such as are currently used for such purposes. In such case, the signal use circuitry includes the receiving circuitry outside the body and associated circuitry, computers, or microprocessors which use the signals for monitoring or for control purposes or may include merely indicator means such as meters, oscilloscopes, oscillographs, electrocardiographs, etc. In many cases, the signals will be used both to operate a device within the body and to operate monitoring means outside the body, so that the signals will be sent both directly to the device in the body and telemetered to outside the body.

In many cases, particularly where signals are transmitted to a location outside the body, the transmission of the signals may not take place on a continuous basis. In such instances, the signal processing circuitry, or the transmission circuitry will include a memory to store signals from the sensor. Generally, the sensor signal will be sampled periodically and the value of the signal at the time sampled stored. Then, when transmission is desired, the information stored in the memory is transmitted. The sampling interval will depend upon the size of the memory and the time periods between transmission of the stored signals. Further, the signals stored may be the "raw data", i.e., signals directly from the sensor, or "processed data", i.e., the processed signal. Of course, there are many other reasons for storing data and ways in which stored data may be used. Also, in some cases, the signal from the sensor may be processed or monitored only at certain intervals, or only in response to inquiry signals that are sent by the signal processing circuitry to the sensor, or in response to signals sent by the signal transmission circuitry or the signal monitoring circuitry to the signal processing circuitry or to the sensor. Thus, where a sensor requires power to produce a signal, power may be supplied to the sensor only periodically in order to conserve a power source such as batteries.

The signal processing, transmission, and use are standard and currently well known in many circumstances.

With the embodiment illustrated, the processed signal is also monitored by signal monitoring circuitry 24 associated with the servicing means. This circuitry may take many forms and its purpose is to determine when the implanted deivce is in need of service. In some instances, the complete absence of a signal from the sensor will indicate need for servicing while in other instances, a signal below or above a certain level, or the presence or lack of signals on a regular or known intermittent basis or after inquiry will indicate the need for servicing.

When the need for servicing is indicated, a signal is sent from the signal monitoring circuitry to the servicing control 25 which initiates and controls the operation of the servicing apparatus 26. For example, if the arrangement of the implantable device and servicing means is such that the device is drawn into a service housing for servicing, as may usually be the case with sensors, the servicing control will first activate means for withdrawing the device from its operable position and moving it into the housing. Such movement may be accomplished in a variety of ways, for example, by use of motors, step motors, solenoids, rotary solenoids, magnets, springs, pressurized fluids, or combinations thereof.

When the sensor is withdrawn into the service housing, means for closing the opening through which the sensor was withdrawn is preferably provided. This may take the form of a septum, door, or valve arrangement. Where the device withdrawn is relatively small and similar to a needle, the septum may merely be a biocompatible elastomeric material through which the device extends, and, when withdrawn, automatically seals the hole. With larger devices, a mechanical type of septum, door or valve such as an iris diaphram arrangement, sliding plates, or a septum with a mechanical clamp or lasso arrangement about the circumference of the septum which forces the septum closed after the sensor is removed, could be used to close the opening when the item is withdrawn. Such septum, door, or valve should be arranged so that the item, when extended, forms a seal to close the housing to the body at that time also.

Once inside the service housing, the control initiates operation of the actual servicing instrumentalities of the servicing apparatus. The servicing instrumentality may take a mechanical form, e.g. brushes or scrapers of various types adapted to be positioned against the device or portion thereof to be cleaned and to rotate or move linearly or in some other fashion to effect a cleaning of the device, or at least the critical portions of the device such as the actual sensing surfaces, or a fluid bath or soak form, e.g. where the device is exposed to an organic or inorganic fluid which dissolves, hydrolyses, depolymerizes or otherwise strips or cleans the device of the build-up of materials. Such exposure may be with or without agitation of some form. The fluid may be chosen from various chemical, detergent or detergent-like solutions; enzyme solutions, which, for example, contain peptidases, collagenases, proteinases, fibrinolytic, or other enzymes; or lytic solutions. Additionally, absorptive, adsorptive, or exchange materials or surfaces could be used in connection with such fluids to rejuvenate them. These surfaces may be provided as the walls to a fluid reservoir or as ion exchange beads or filaments or other absorbing, adsorbing, or exchanging surfaces located in the housing either in direct continuous contact with the fluid, or located for intermittent contact with the fluid when needed. For example, a strip of ion exchange material could be wound between a supply and take up spool and such exchange material taken from the supply spool and drawn into contact with the fluid when needed to regenerate it. Further, fluids could be used to dilute out or otherwise remove unwanted or undesirable embedded molecules from poisoned or plugged membranes or other surfaces.

Other forms of the servicing instrumentality could be pumps or other means for generating pulsating motions of fluid, electrodes for electrical cleaning or rejuvenating, ultrasonic cleaning equipment, or heating or cooling equipment, or a combination of several of the methods discussed.

For some devices, cleaning or rejuvenating of the device itself will not be possible and the device, or at least the active portion thereof, such as the sensing tip, will actually need to be replaced. In such instance, the servicing instrumentality of the apparatus will take the form of a replacement apparatus where the old device or portion thereof is removed and a replacement installed. For use with a sensor, the sensing surface may take the form of a sensing tip which may be slid from the sensor base while a new tip is slid into place.

Also, with some devices which may be controlled or operated electronically, it may be possible or desirable to re-educate the device such as by reprogramming the memory so that the device can perform additional, new, different, or modified functions or by connecting or triggering circuitry in the device which was previously dormant, again so that the device can perform additional, new, or different functions. This re-educating can be accomplished in various ways within the service housing.

After servicing of the device is complete, the device is moved from servicing position in the housing to its extended, operational position in the body.

If the arrangement of the device and servicing means is such that the servicing apparatus or servicing instrumentality is moved from a service housing into servicing position, the signal from the control will initiate movement of such servicing apparatus or instrumentality from the housing. This movement may be accomplished by any of the methods described above while the opening through which the apparatus leaves the housing could be a septum, door, or valve as previously described.

For example, where a catheter is to be cleaned, it may be desirable in some circumstances for the servicing instrumentality to extend from the housing into the catheter rather than drawing the catheter into the housing. In such instance, the opening in the housing may be connected to the catheter through a Y-type connector and an obturator passed through a septum or other seal from the housing into the catheter. The obturator may be a small coated or uncoated wire which is coiled on a spool within the housing. The spool may be connected to a motor so that when cleaning is desired, the motor operates to unwind the wire and extend it into the catheter. After desired extension, the rotation of the spool is reversed to rewind the wire thereby drawing it back through the catheter into the housing.

If the arrangement of the device and service housing is such that a portion of the servicing means is built into the device or is permanently positioned in servicing juxtaposition to the device, the signal from the control will initiate operation of such servicing means.

For example, where a catheter is provided with means for changing its internal shape or moving its internal walls to losen and break up any material which is blocking the catheter, means in a service housing will be operatively connected to the catheter to cause such change or movement. For a catheter with a mechanical cleaning instrumentability built into the catheter or located inside the lumen, means in the service housing will be operatively connected to such mechanical cleaning instrumentality to cause its operation.

In many instances, after or during servicing, it may be necessary to dispose of waste products generated as a result of servicing. If so, waste disposal means 27 are provided. For example, when a liquid is used for cleaning a device, after one or more cleanings, the liquid may become "dirty" or spent so that it can no longer be effectively used for subsequent cleanings. In such case, the liquid will need to be recharged or replaced. In a completely implantable unit, this may be done by keeping the liquid in a reservoir within the housing which has a septum or membrane through which a hypodermic needle may be passed. Thus, a needle is passed through the skin of the body in which the device has been implanted and through the septum or membrane into the reservoir. The spent liquid is then withdrawn from the reservoir and new liquid injected into it. Where an ion exchange or other absorptive, adsorptive, or exchange process is used, it may be necessary to rejuvenate the exchange material periodically. This may be done, again, by withdrawing and injecting various fluids into a reservoir, or the exchange material itself, such as small beads, may be exchanged through a similar arrangement with a hypodermic needle. If the exchange material is in the form of an elongate thread or filament, it may also be threaded through a needle from and to the device, or through some other type of opening or communicating passage. Where the unit is only partially implanted in the body so that a portion of it opens to outside the body, or where communication from the unit through the skin to outside the body by means of a catheter or other biocompatible passageway is provided, waste removal from the housing, and/or resupply of material to the housing may be accomplished through such outside connection.

Rather than removal of material from the housing to outside the body, in some instances it may be appropriate to discharge or eject waste material from the housing through a catheter or other opening into the blood stream of the body, the bladder, the gastrointestinal tract, the lymphatic system, or to other areas of the body to be disposed of by natural means, or natural body functions.

The block diagram of FIG. 1 is a generalized diagram of an embodiment of the invention which contains some features of the invention which are not necessary in all applications. Thus, in some applications, because waste can be satisfactorily stored in the housing, waste disposal will not be a problem and will not be necessary. Also, in some applications, rather than monitoring the signal from a sensor or other device to determine when servicing is necessary, the servicing control may include a timer which causes the servicing apparatus to operate periodically at predetermined time intervals, or such control may include trigger means operable from outside the body such as by telemetry, magnetics, or other means, so that operation of the servicing apparatus is initiated from outside the body.

Where the device to be serviced is other than a sensor, a different arrangement as to signal processing, transmission, use, and monitoring of the signal may be used. For example, when used with a catheter such as may be attendant to a drug pump, the device to be cleaned, i.e. the catheter, does not generate electrical signals. If some type of sensor is used in conjunction with the catheter to monitor its condition, such as a pressure transducer or flow indicator to indicate catheter blockage by an increase in pressure or decrease in flow in the catheter or within the pump device, a similar arrangement as shown may be used with such sensor indicating the condition of the implantable device. However, in those instances, there may be no signal transmission or use other than the signal monitoring to determine when servicing is necessary. If the implantable device has no such sensors, and servicing is done on a periodic or other basis, there may be no signal processing, transmission, use, or monitoring.

It should be noted that although not indicated in the drawing, various forms of feedback from various blocks to other blocks may be desirable and may be provided. Thus, as indicated above, signals may be sent from the signal transmission circuitry or the signal monitory circuitry back to the signal processing circuitry or the sensor when information is desired, or when error signals appear and error checks are made, or for various other reasons. In addition, feedback may be used between the service control and the servicing apparatus to indicate position of the device being serviced, position of the servicing apparatus, extent of servicing completed and various other parameters. Further, feedback from the waste disposal or servicing apparatus could indicate when disposal or regeneration is necessary and regeneration can be controlled by the service control, or a signal indicating necessity of disposal or regeneration could be transmitted to outside the body by the transmission means. While various forms of feedback are suggested here, it will be obvious that any type of circuit operation and any type of feedback necessary or desirable for such operation may be provided.

As shown in FIGS. 2 through 4, one embodiment of the invention is for use with and includes a sensor 30 adapted to be implanted in a living body so that the sensing surface 31 is positioned in a blood vessel 32 in contact with the blood flowing therein. Many types of sensors could be used in such manner, for example, glucose sensors, pressure sensors, or sensors that detect certain materials or ions in the blood. When these sensors are implanted in a blood vessel, blood may begin to clot about the sensor and gradually build up thereon or the sensor may suffer from other adverse effects due to chemicals or molecules in the blood. This affects the sensing capability of the sensor so that the output of the sensor gradually changes and eventually an accurate signal from the sensor can no longer be obtained. At this point, the sensor would generally have to be removed and replaced. Such replacement might be necessary for some sensors as often as every several weeks.

With the current invention, sensor 30 is positioned in a housing 33 with the sensing surface 31 of the sensor extending through an opening 34 in cannula-like portion 35 of the housing which is sealed with septum 36. End 35a of housing portion 35 is adapted to be secured to the blood vessel 32 in an appropriate manner such as by stitching or gluing, so that when sensing surface 31 extends therefrom through septum 36 as shown in FIGS. 2 and 3, it is in direct contact with the blood.

Housing 33 contains a servicing chamber 37 formed by walls 38, and bottom 39 through which sensor 30 can be moved so that sensing surface 31 can be withdrawn from the blood stream, through septum 36, and into servicing chamber 37 for servicing. Sensor 30 may be mounted for movement in various ways. As shown, a motor unit 40, which may be a micromotor or stepper motor as manufactured by Portescap U.S., Worcester, Pa., is mounted inside housing 33 in suitable manner, such as by welding, screwing, or glueing tabs 41, which extend from motor unit 40, to a wall of housing 33. A shaft 42 extends from motor unit 40, with its distal end held in place by bracket 44, also secured to a wall of housing 33.

A gear 45 is secured to shaft 42 and engages a rack 46 which is secured to the end of sensor body 30. Thus, when gear 45 rotates in one direction, rack 40 and sensor 30 are drawn from extended position into the housing as shown in FIG. 4, and when gear 45 is rotated in the opposite direction, sensor 30 is moved from the housing to its extended position as shown in FIGS. 2 and 3. Bracket 44 has arms 47 extending therefrom, which hold rack 46 in place against gear 45. In this way, shaft 42, gear 45 and rack 46 are held in relative position to ensure engagement of gear 45 in rack 46. O-rings 48 are provided in cleaning chamber bottom 39 to ensure a good fluid seal about sensor 30.

When sensor 30 is withdrawn into the housing, it is drawn through septum 36 which closes opening 34 as sensor 30 is pulled therethrough. The septum may be made of a biocompatible elastomeric material which compresses as sensor 30 passes through it and expands to its closed position shown in FIG. 4 when sensor 30 is removed, to thereby close opening 34. A backup, semiflexible diaphragm 49 and associated springs 50 may be provided, as shown, as a second closure for opening 34. In most case, where sensor 30 is small and needle like, the septum will close satisfactorily so no additional door or valve will be necessary.

A fluid reservoir 55 formed within housing 33, is connected to servicing chamber 37 by means of supply tubing 56 and liquid pump 57 and by return tubing 58. A filter 59 is provided at the end of tubing 56 in reservoir 55.

Wires 60 from the sensor extend through the housing as shown to the portion indicated generally as 61 of the housing which contains the signal processing circuitry and the signal transmission circuitry as described above for FIG. 1. This circuitry may monitor the signals produced by the sensor, store such signals, and transmit them by means of standard telemetry circuitry to a receiver outside the body. Circuitry to perform these functions is well known and will be obvious to one skilled in the electronics art concerned so is not shown in detail here.

Rather than the wires 60 extending from the sensor, the sensor itself could contain its own power source, such as a small battery, and a small radio transmitter which would transmit signals from the sensor to the signal processing or monitoring circuitry.

The servicing control circuitry is housed in the portion indicated generally as 62 of the housing. This control circuitry will also include the signal monitoring circuitry or other circuitry such as clock circuitry or telemetry control circuitry which initiates operation of the servicing control circuitry. Again, such circuitry is well known in general and the specific circuitry needed will be obvious to one skilled in the electronics art concerned from the description of the operation of the servicing apparatus.

When servicing of the sensor is desired, either because the signal from the sensor, as monitored by the monitoring circuitry, indicates that the sensor's performance has become substantially degraded, because the signal from the sensor as transmitted to outside the body shows that the sensor's performance has become substantially degraded, because of some other indication that the sensor's performance has become substantially degraded, or because servicing is done on a periodic basis and the time for servicing has arrived, servicing is initiated by the servicing control circuitry.

When servicing is initiated, either automatically by the servicing control or by the servicing control being triggered from outside the body, the control causes motor unit 40 to operate and withdraw sensor 30 into housing 33 where sensing tip 31 is within servicing chamber 37. Operation of motor unit 48 may be timed so that it operates for a sufficient period to insure that sensor 30 has moved to fully withdrawn position as shown in FIG. 4 before actual servicing begins and that it is fully extended when servicing in completed, or other sensors, such as position sensors, may be provided to indicate when sensor 30 is fully withdrawn or fully extended. Rather than the additional position sensors, sensors on the motor unit could monitor rotation of shaft 42 to obtain similar sensor position information.

With sensor 30 in withdrawn position so that sensing tip 31 is in servicing chamber 37, the servicing control circuitry causes operation of pump 57 to circulate liquid from the reservoir 55 through supply tubing 56, servicing chamber 37 and back through return tubing 58 to the reservoir. Filter 59 prevents suspended material in the liquid from being recirculated into servicing chamber 37, or from passing through and thereby possibly clogging the pump. The fluid may be of a variety of types as mentioned above. If some type of absorptive or adsorptive material is used to regenerate spent fluid, it may be provided in the form of microbeads 65 in reservoir 55. Satisfactory microbeads may be any one of a variety of those manufactured by Polyscience, Inc.

Pump 57 may be operated for a set period of time which has been determined to be sufficient to clean and recondition the sensor, may be operated for a period otherwise previously determined, or the period of operation may be determined as cleaning is taking place. After completion of cleaning, the servicing control causes operation of the pump to cease and operates motor unit 40 to extend sensor 30 into operable position where it remains until further servicing is needed.

Power for operation of the unit may be provided in several ways. Standard batteries such as currently used with pacemakers may be located in a portion of the housing, such as the area generally indicated at 66, some type of energy coupling means could be utilized to couple energy from a source outside the body to the unit, or wires could extend from a power source outside the body, through an opening in the skin, to the unit.

After several servicings of the sensor, the liquid used for servicing may become full of suspended matter or may otherwise become spent or unfit for further servicing use. In such instance, the liquid may be replaced by inserting a hypodermic needle through the skin and through septum 67 into reservoir 55. The old liquid can be withdrawn through the needle and replaced with new liquid. O-ring 68 insures a good seal for septum 67. Where microbeads are used in the reservoir, these, too, may be withdrawn through the needle and replaced with new microbeads.

Figure 6:
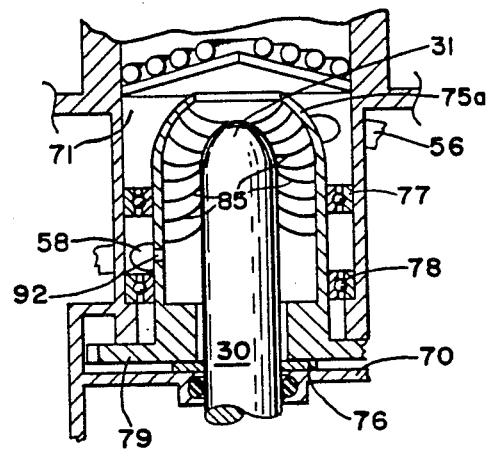
Figure 7:
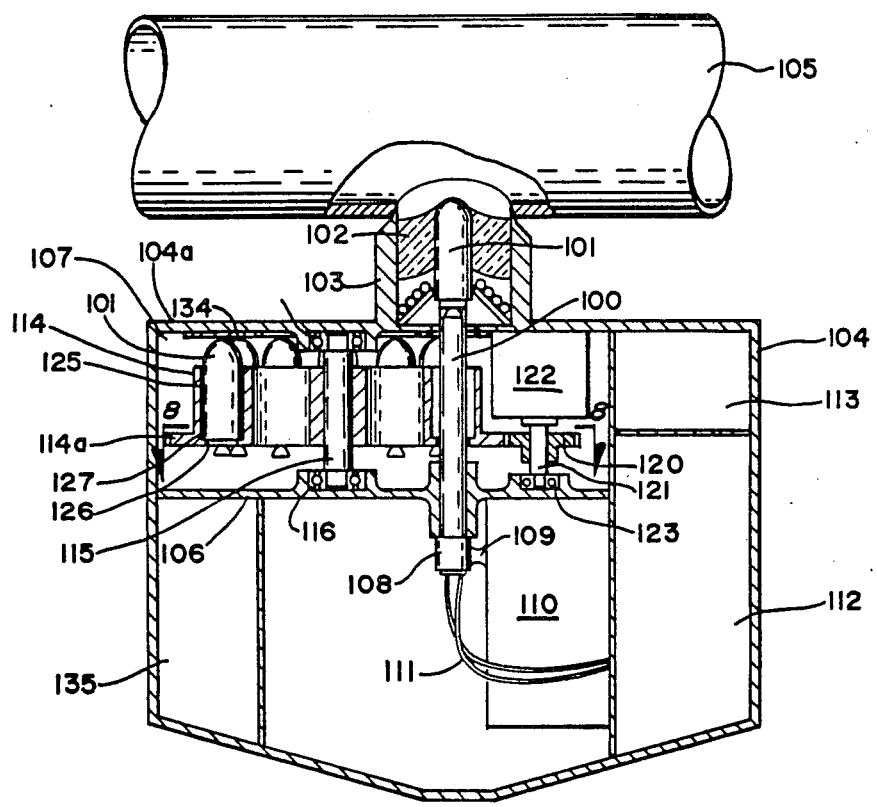
Figure 8:
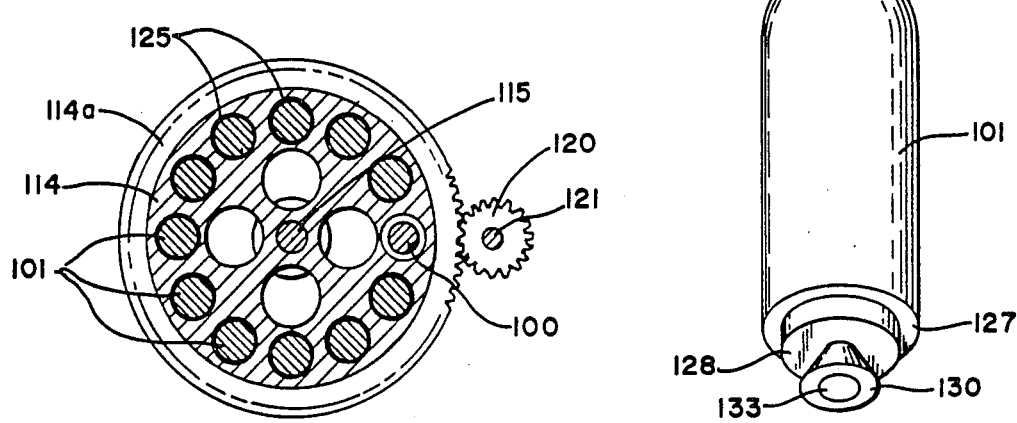
Figure 9:
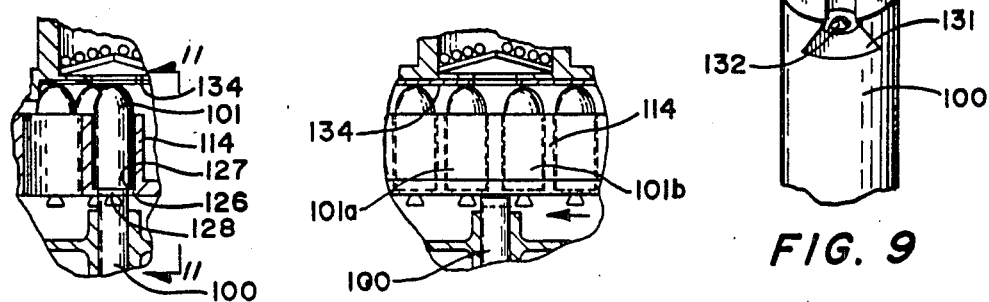

FIGS. 5 and 6 show a second embodiment of the invention, again illustrated as a unit specifically for servicing a sensor. Parts common to the units shown in FIGS. 2 through 4 and 5 and 6 carry the same reference numbers. Thus, sensor 30 is again mounted in and as part of housing 33 so that it extends from portion 35 of housing 33 through septum 36 into the blood stream carried by blood vessel 32.

In the embodiment of FIGS. 5 and 6, sensor 30 extends through bottom wall 70 of servicing chamber 71 and is supported by a sleeve 72 secured thereto. Sleeve 72 is secured to arm 73 extending from a stepper motor unit 74 secured in an appropriate manner to a wall of housing 33. In this embodiment, stepper motor unit 74 has internal gearing and drive such that arm 73 moves up and down along the side of the unit thereby moving sensor 30 up and down within the unit. Rather than the servicing chamber merely providing for fluid contact between a fluid and the sensing portion 31 of the sensor, in the embodiment of FIGS. 5 and 6, mechanical cleaning means for the sensor are provided. Thus, within cleaning chamber 71, a brush housing 75 is concentrically mounted for rotation about sensor 30 on a teflon bearing washer 76 and is held in place in the chamber by sealed bearing 77 and 78. The lower portion 79 of brush housing 75 extends outwardly and is configured to form a gear. A mating gear 80 secured to shaft 81 of motor 82 rotates to thereby cause rotation of brush housing 75. Brush bristles 85 extending from the interior walls of brush housing 75 rest against sensor 30.

Wires 86 extend from the sensor to a take up reel 87 secured to wall 88 of the housing by bracket 89 and powered by motor 90 so that as the sensor is lowered by motor unit 74, take up reel 87 winds wires 86 thereon, and as the sensor is raised by motor unit 74, the take up reel 87 unwinds wires 86. In this way, the wires 86 are kept relatively tight and out of the way. Wires 91 extend from take up reel 87 where they connect through a normal slip ring electrical contact, not shown, to wires 86, to the signal processing circuitry 61 or other appropriate circuitry as described.

When servicing is desired, the servicing control located at 62 causes operation of stepper motor unit 74 which withdraws sensor 30 into servicing chamber 71 and brush housing 75, as shown in FIG. 6. The servicing control then causes operation of motor unit 82 which rotates brush housing 75 about sensor 30 thereby mechanically brushing built up material from the sensor. It should be noted that brush housing 75 extends above sensor 30 in its retracted position and curves as at 75a so that bristles 85 press against the sensing end 31 of sensor 30.

In many cases, the brushing action of bristles 85 will be sufficient to clean the sensor so that it may be extended again after brushing for another period of operation, and such brushing will not build up an unmanageable amount of debris in the brushes to prevent satisfactory further operation. In some instances, however, the brushing operation will build up material in the brushes that will need to be removed prior to the next brushing operation, or the sensor will need a fluid treatment to reactivate its sensing surface after it has been cleaned, or to loosen or otherwise treat the material on the sensor prior to, during, or after brushing. For this purpose, housing 33 may be provided with the fluid reservoir 55, supply pipe 56, pump 57, and return pipe 58, as described in reference to FIGS. 2 through 4. With such arrangement, fluid can be circulated through servicing chamber 71 and through brush housing 75 with sensor 30 in either extended or retracted position to clean debris from brush bristles 85, or the fluid can be circulated with sensor 30 in retracted position for fluid treatment of sensing surface 31. Fluid can enter brush housing 75 through the top and leave the housing through holes 92 in the lower portion thereof.

It should be noted that while the fluid supply and circulation system is shown, if fluid treatment is not necessary in connection with the mechanical treatment, such fluid treatment system need not be present, and if not present, leaves more room for various mechanical treatment apparatus that could be used.

FIGS. 7 through 11 illustrate a third embodiment of the invention where the sensing tip of the sensor is replaced rather than cleaned.

A sensor base 100 has a detachable sensing tip 101 extending through septum 102 in cannula-like portion 103 of service housing 104, into the blood stream carried by blood vessel 105. Sensor base 100 extends through a hole in floor 106 of exchange chamber 107 and is supported by a collar 108 attached by arm 109 to stepper motor unit 110. As in the embodiment of FIGS. 5 and 6, stepper motor unit 110 has internal gearing and a drive so that arm 109 moves up and down in the motor unit, thereby moving sensor base 100 up and down in the housing. Wires 111 extend from the sensor to the signal processing and other circuitry located in the housing at 112. The servicing control and related circuitry is located at 113.

A sensor tip tray 114 is mounted for rotation on axle 115 between exchange chamber floor 106 and the upper housing wall 104a by means of bearings 116 and 117. The lower portion 114a of the tray 114 forms a flange with gear teeth cut therein and adapted to mate with gear 120 mounted on motor shaft 121 of motor 122 which is secured to the upper wall of housing 104. The distal end of shaft 121 is held in place by bearing 123.

Sensor tip tray 114 has a plurality of wells 125 in which sensing tips 101 are positioned. Each well has a shoulder 126 at its bottom which supports mating shoulder 127 of the sensor tip. A portion 128 of sensor 101 of reduced diameter extends through reduced diameter bottom portion of well 125 and stops flush with the bottom of tray 114. A cone extension 130 of sensor tip 101 extends below the bottom of tray 114 and is adapted to mate with receiving slot 131 in the top of sensor base 100. A spring loaded ball 132 mates with depression 133 in the bottom of conical extension 130 to thereby hold the tip 101 in place on sensor base 100 and to provide an electrical contact in well known manner between the base and tip which is insulated from the surrounding portion of both the base and tip. The second electrical contact is between the conical surface of the conical extension and its mating surface in the groove.

Figures 10, 11:
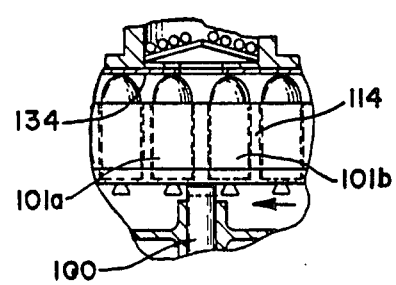

In operation, when the sensor needs servicing, the servicing control causes motor unit 110 to operate to withdraw the sensor into the service housing. The sensor will be withdrawn until the sensor tip 101 rests in tip tray 114 as shown in FIG. 10 with the top of sensor base 100 just below the bottom of the tray. When in this retracted position, the control causes operation of motor 122 which rotates tray 114. As tray 114 rotates, sensor tip 101 is slid out of position on top of sensor base 100 and the next tip in line on the tray is slid into place with cone portion 130 sliding into groove 131. FIG. 11 shows the tray 114 as it is rotated, midway between its stops. Thus, in FIG. 11, service tip 101a has just been removed from sensor base 100 as tip 101b is moving into position to be slid into place on the base. When the new sensor tip is in position, rotation of the tray stops and motor unit 110 is activated to again extend the sensor. In extended position, the sensor base 100 extends through the well 125 in the tray from which the new sensor tip has been obtained.

While references have been made to top and bottom, it should be realized that those references are in regard to the orientation of the service housing shown, since in actual practice, the housing may be implanted in a number of different orientations and the orientation will change depending upon the position of the person in which it is implanted. In order to maintain the tips in position in the tray regardless of housing orientation, a plastic liner 133 is provided on the inside of housing wall 104a above the tray so that the tips rub against it and are held firmly in the wells.

Batteries or other energy source as described may be located in the area indicated as 135.

Figure 12:
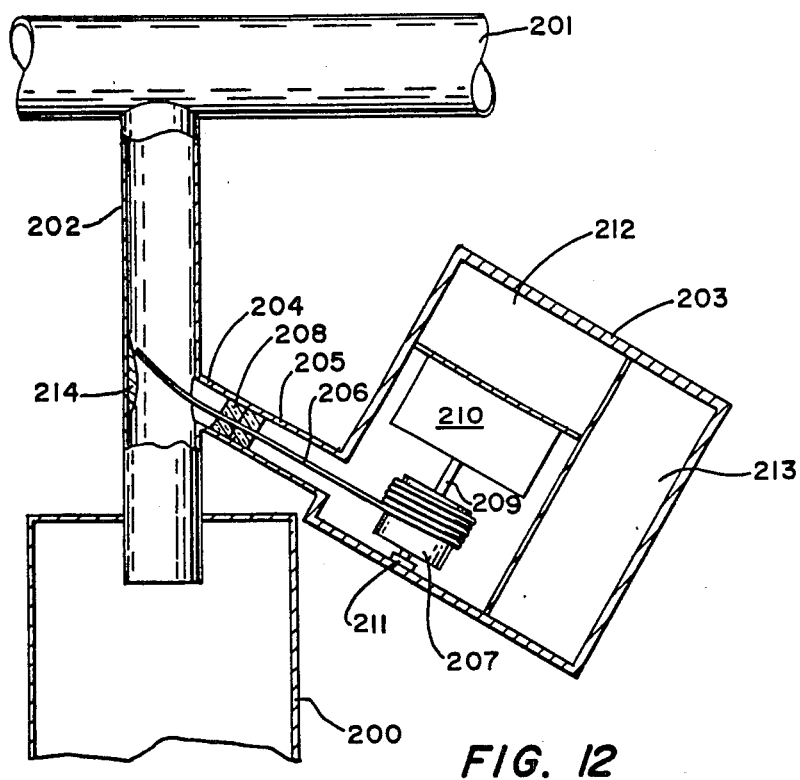
Figure 13:
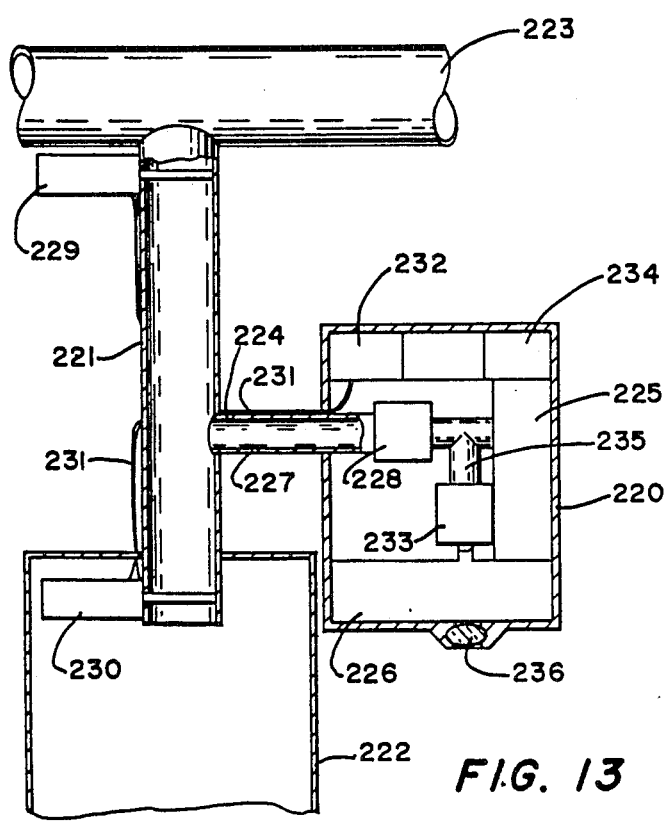

FIGS. 12 and 13 show embodiments of the invention where the servicing means is located in a service housing and the service housing and device to be serviced are arranged so that the servicing means extends from the housing into servicing position with respect to the device, rather than the device being drawn into the housing for servicing.

FIG. 12 shows a drug pump 200, such as an insulin pump, connected to a blood vessel 201 via catheter 202. The drug pump 200 is shown schematically as a housing with a catheter. None of the normal internal workings of the pump are shown since they will be well known to those skilled in the art and they form no part of the invention. With pump 200 in operation, insulin is pumped through catheter 202 into the blood stream. A current problem with insulin pumps is that the insulin, after storage for a period of time, tends to precipitate as it passes through a catheter. The precipitate builds up in the catheter and eventually obstructs it to a substantial degree so that the pump is rendered ineffective for further delivery of insulin.

As illustrated, a service housing 203 is connected to catheter 202 by means of Y-type connector 204 and passageway 205. An obturator wire 206 extends from a spool 207, through passageway 205 and through a septum 208. Spool 207 is mounted for rotation on shaft 209 which extends from motor 210 to bearing bracket 211 which is secured to a wall of service housing 203. An energy source such as batteries located in the housing at 212 supplies power to motor 210 and to the servicing control circuitry located at 213 which controls operation of motor 210.

When it is desired to clean catheter 202, motor 210 is operated to rotate spool 207 in a direction to unwind wire 206 thereby causing it to move through septum 208 and into catheter 202. A protective patch 214 of a hard material is provided in catheter 202 opposite the entrance of passageway 205 through the Y-type connector to prevent puncture or abrasion of catheter 202 by obturator wire 206 as it extends and moves into catheter 202. It also serves to direct obturator wire 206 down the length of catheter 202. Spool 207 is operated to unwind sufficiently so that obturator 206 extends through catheter 202 to dislodge any blockage. The motor is then reversed and the obturator wire again wound on the spool so as to withdraw the wire from catheter 202. Wire 206 preferably rests right at the edge of septum 208 so that the end does not extend into catheter 202 or any portion of the Y where flow of solution from the pump passes so that such end cannot form a nidus point for further crystallization and precipitation of the material being pumped.

The obturator wire may be a solid, substantially straight wire of spring steel or other appropriate material, or may be formed of wound or coiled wire in a manner similar to a drain cleaner. It may also take other forms such as twisted wire strands or wire wound on some type of core, either solid or hollow, and may be coated with a material such as teflon, or be uncoated. It may also be advantageous to rotate the obturator as it is being extended through the catheter, or when it reaches its extended position.

With the Y-type arrangement as shown, the portion of catheter 202 which extends from the Y into the pump is not cleaned by the extension of obturator 206. It thus may be desirable to provide a flexible or jointed Y-type connector so that it and service housing 203 can be moved to enable the obturator to be extended through catheter 202 toward the pump, or a configuration may be provided so that the obturator enters catheter 202 substantially at its end within the pump so that the obturator can be extended through substantially the entire length of the catheter.

FIG. 13 shows a second embodiment for use with a drug pump and catheter arrangement, or any similar arrangement of a catheter. In this embodiment, service housing 220 is connected to catheter 221, which extends between drug pump 222 and blood vessel 223, by means of Y-type connector 224. A fluid pump 225 is located in service housing 220 in communication with a fluid reservoir 226 and passageway 227 which connects through Y-type connector 224 to catheter 221. An electrically operated valve 228 is provided in the service housing in passageway 227 and electrically operated valves 229 and 230 are provided at opposite ends of catheter 221. Wires 231 extend from the control circuitry located within housing 220, as at 232, to valves 229 and 230 to operate them as necessary. Additional wires, not shown, will extend from the control circuitry to valves 228 and 231 to operate them as necessary. A power supply, such as a battery, may be located in the housing at 233.

When cleaning or servicing of catheter 221 is required, a valve 231 located in passageway 232, which extends between pump 225 and reservoir 226, is opened to allow pump 225, which is here described as a syringe type of pump, to draw fluid from the reservoir into its internal reservoir. Valve 231 is then closed and valves 229 and 230, which are normally open to allow medication to pass therethrough from the pump to the blood stream, are closed by the control circuitry and valve 228, which is normally closed, is opened. Pump 225 is operated to pump the cleaning fluid from its internal reservoir into catheter 221. The cleaning fluid is of a type that will dissolve or suspend the build-up of material in catheter 221. Depending upon the type of build-up to be removed and the type of cleaning fluid used, the fluid may merely be pumped into catheter 221 and allowed to sit there to dissolve the deposits blocking the catheter, or the fluid may be pressurized to some degree by the pump, or alternately pressurized and depressurized to create a type of turbulence within catheter 221 to aid in dissolving or breaking up the deposits. After fluid treatment of the catheter for a period sufficient to dissolve or break up and suspend the blockage, the fluid is withdrawn back into pump 225, valve 228 is closed and valves 229 and 230 opened so that the drug pump 222 can again function in normal manner. The fluid held in the pump may continue to be held there, or valve 231 may be opened and the fluid returned to the reservoir.

If more fluid is required in the catheter than can be held in the internal reservoir of the pump, the pump and valves will be operated so that when all fluid from the pump has been pumped into the catheter, valve 228 will close and valve 231 will open so that additional fluid from the reservoir 226 can be drawn into the pump. When the pump reservoir is again filled, valve 231 is closed and valve 228 opened so that the fluid from the pump is again pumped into the catheter. This procedure may be repeated as many times as necessary to get the desired amount of fluid into the catheter. When fluid is pumped from the catheter, the procedure is reversed so the fluid is pumped back into reservoir 226.

Rather than using electrically operated valves, the valves could be fluid operated and operate from a fluid pump in the housing, or from some other source of pressurized fluid in the housing. Further, with some drug pumps it will not be necessary to provide valve 230 since these pumps provide a one-way valve in the catheter to prevent any backflow of material. This one way valve would perform the function of valve 230, blocking the catheter to backflow of solution into the pump.

Fluid reservoir 226 is provided with a septum 234 which can be accessed from outside the body by means of a hypodermic needle so that spent fluid in the reservoir may be withdrawn and replaced by fresh fluid.

The apparatus shown in FIG. 13 may very easily be used for an open system in which a catheter may be cleaned or otherwise serviced by merely injecting a fluid into the catheter so that it flows with the other fluid in the catheter, such as the insulin, into the body, by merely leaving out some or all of the valves 228, 229, and 230. Thus, pump 225 would merely pump fluid from reservoir 226 into catheter 221 when necessary to dissolve build-up of material. This fluid could be pumped in at the same pressure as the fluid from the drug pump, or could be at a higher pressure or in pressure pulses so as to dislodge or break up any catheter blockage. Fluid reservoir 226, which in this case would be continually depleted, would be filled when needed via a hypodermic needle extended through septum 234 as described.

While the fluid could merely be added to the catheter through the Y-type connector as shown in FIG. 13, other means of introducing the fluid could be used such as a small additional catheter which could be placed within the larger catheter to be cleaned so that the opening from which the servicing fluid is discharged is adjacent an area of the catheter likely to need servicing, or such smaller catheter can be made to be moved within the larger catheter so that the servicing fluid, which may be under pressure, is applied when and where needed.

Further, with either the closed or open system described, a heating unit could be provided within the housing if it is found to be advantageous to heat the fluid prior or during servicing.

FIGS. 14 to 22 show embodiments of the invention where a portion of the servicing means is built into and included as a portion of the device to be serviced and that portion of the servicing means is operated by the remainder of the servicing means which may be located in a service housing apart from the device, or may be located in a housing along with the device.

FIG. 14 shows a drug pump 250 connected to blood vessel 251 via catheter 252. Located within the lumen of catheter 252 is a flexible tube member 253 which is held in place by crossmembers 254 secured in catheter 252. These crossmembers may be glued in place or may be made slightly larger than the diameter of the catheter lumen so that they are bent or compressed slightly when put into place. The purpose of the crossmember is merely to hold the inner flexible tube member in place so that it is not displaced by normal flow of fluid through the catheter. It should be realized that there are many ways the tube member could be held in place such as by attaching it by glue or heat treatment to one side of the catheter lumen.

Tube member 253 is connected by passageway 255 and valve 256 to a pump 257 in service housing 258. Pump 257 is of the type having an internal reservoir, such as a syringe type of pump, and is connected to a motor or other power source 259. The service control and other required circuitry is located in the housing at 260 while a battery or other energy supply may be located at 261.

When servicing is necessary, the servicing control operates the motor 259 causing the pump to operate to pump fluid from its internal reservoir into tube member 253, thereby causing it to expand into the catheter lumen. This expansion will break up any blockage thereby cleaning the lumen. After expansion, the pump is reversed so that the fluid is drawn back into the reservoir collapsing tube member 253. The pump can be controlled to cycle once, or to cycle several times for each servicing so as to ensure breakup of large blockage. With several cycles, the pump can pump more fluid into the tube member each time, thereby starting with only a small expansion and increasing the expansion progressively. Valve 256 is provided to prevent any leakage from pump 257 into tube member 253 between servicing so it will be closed between servicing but open during servicing.

A slightly different embodiment of a similar system is shown by FIG. 16. As shown, catheter 270 has a flexible inner lumen wall 271. The passageway 255 from service housing 258 of FIG. 14 connects to the area between the main catheter wall. Thus, catheter 270 is a replacement for catheter 252 of FIG. 14.

With the embodiment of the catheter shown in FIG. 16, when fluid is pumped between catheter wall 270 and inner wall 272, the inner wall expands into the catheter lumen thereby dislodging and breaking up any blockage.

FIG. 17 shows a catheter arrangement with catheter 280 extending between pump 281 and blood vessel 282. Catheter 280 has been specially built to have a wire 283 therein extending along its length on one side of the lumen. Either at one end of the wire, or intermediate its length, as shown, the wire is connected to means to cause it to rotate, such as gear 284. Service housing 285 is located adjacent gear 284 and has a mating gear 286 secured to shaft 287 of motor 288.

When servicing is necessary, servicing control circuitry located within the housing as at 289 causes operation of motor 288 which will rotate wire 283 within the catheter lumen.

The wire 283 may be made of various materials or may merely be a rod rather than a wire, and may have other wires or bristles 291 extending therefrom which act as brushes when wire 283 is rotated to clean the lumen, or the wire 283 itself may whip around or spiral around in such manner that it will break up and dislodge any catheter blockage. Again, the power source may be batteries held in the housing at 292.

FIG. 18 shows a catheter 300 connecting drug pump 301 with blood vessel 302. In this embodiment, a portion of the servicing means, indicated generally at 303, is built into drug pump 301. In this way, a wire or rod 304 extends into catheter 300 from its end within drug pump 301. Again, none of the normal internal parts of the drug pump are shown. The servicing means located within the drug pump housing 301 is partially illustrated and will include the various components as illustrated in the service housing of FIG. 17.

Rod 304 is connected to a motor 305 which operates when servicing is necessary to rotate rod 304 to thereby clean catheter 300. The various other components of the servicing means such as the control circuitry and power supply, will be included within pump housing 301.

Figure 19:
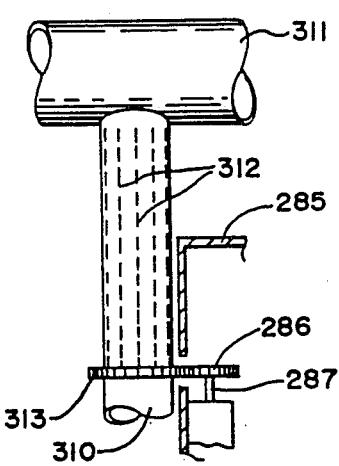

FIG. 19 shows a catheter 310 and blood vessel 311 arrangement similar to that of FIG. 17, but rather than an internal wire or rod in the catheter, a sereis of relatively stiff wires 312 are spaced circumferentially in the wall of catheter 310. The lower ends of the wires 312 are secured to a ring 313 which extends from the catheter and has teeth formed on at least a small circumferential portion which engages gear 286 extending from a service housing 285. The service housing is the same as that shown in FIG. 17.

When servicing is required, ring 313 is rotated by gear 314 a slight amount to twist catheter 310 to thereby loosen and dislodge any blockage therein.

Figure 20:
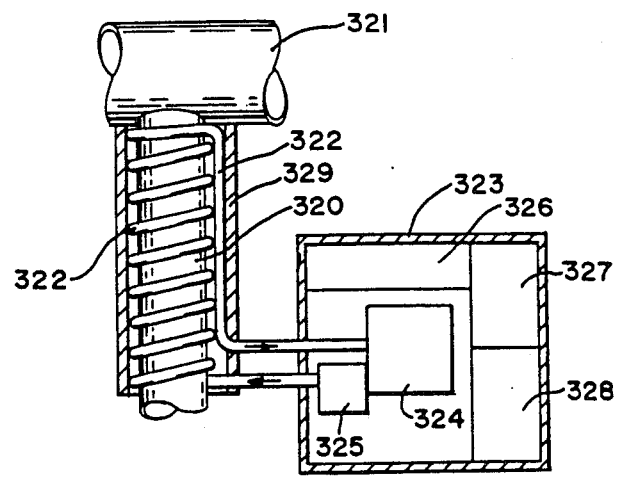
Figure 21:
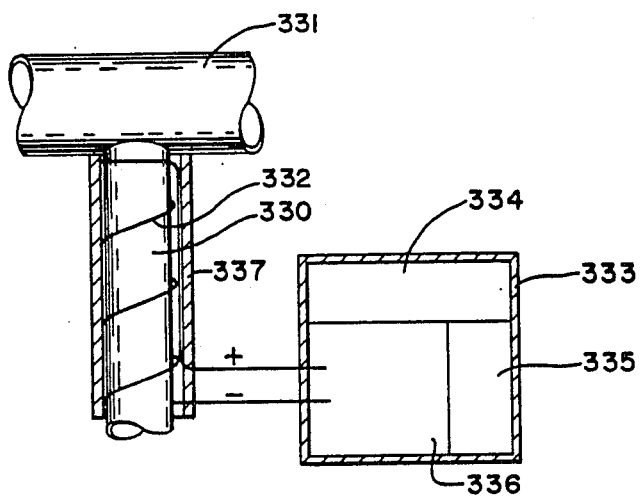

In some cases, a mere heating of the catheter will be enough to dissolve any material built up therein, and, if the heating is not extreme, such heating will not harm the body. FIGS. 20 and 21 show catheters arranged to be heated.

FIG. 20 shows catheter 320 connected to blood vessel 321. A hollow tube 322 is coiled about catheter 320 and is adapted to be connected to servicing means in a service housing 323 which will supply and circulate a heated fluid through tubing 322. For this purpose, service housing 323 has a fluid pump 324 and fluid heating unit 325 connected to tubing 322. No reservoir is necessary in this closed system since fluid is continually recirculated during servicing. The housing 323 also contains a power supply at 326, control circuits at 327, and monitoring circuits at 328, all as previously described. An insulating sheath 329 surrounds heating tube 322 so it does not come in direct contact with the body.

FIG. 21 shows catheter 330 connected to blood vessel 331. A heating filament 332 is wrapped about the catheter and is connected to a service housing which supplies electrical current to the filament to cause it to heat catheter 330. For this purpose, device housing 333 need only contain a source of power located at 334, monitoring circuitry at 335, and control circuitry at 336. Since an electrical output is required for this embodiment and the embodiment of FIG. 22, the control circuitry itself can generate and supply the required outputs. Again, insulating sheath 337 surrounds the catheter and heating filaments and shield them from direct contact with the body.

Figure 22:
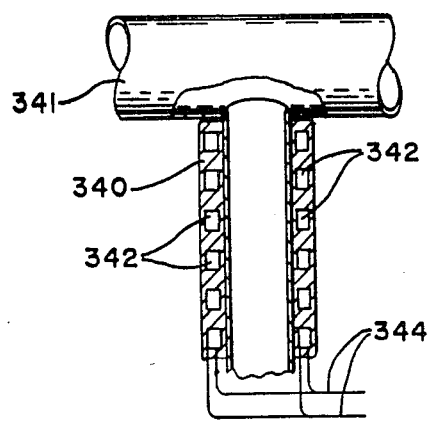

FIG. 22 shows an arrangement of a catheter 340 attached to blood vessel 341. Electromagnets 342 are embedded in opposite sides of the catheter wall. Wires 344 extend from the electromagnets to a service housing such as 333 shown in FIG. 21 which provides electrical current to the electromagnets when it is desired to magnetize them. When servicing is required, the control circuitry causes the electromagnets to be energized, creating magnetic fields between opposing pairs of magnets. These magnetic fields will cause the catheter to distort, thereby breaking up any blockage therein. The control circuitry could be adapted to alternately cause the magnet pairs to attract and repel thereby tending to increase the distortion of the catheter.

Rather than using pairs of electromagnets which can be made to attract or repel, a pair made up of an electromagnet and a piece of magnetic material, such as iron, may be used. In such case, when the magnet is energized, it will attract the magnetic material, again distorting the catheter.

Rather than electromagnets, electrodes could be embedded in the walls of catheter 340. In such case, the servicing means provides a voltage to opposing electrode pairs to form an electrical field between them. This electrical field causes electrophoresis of the material built up in the catheter to thereby dissolve or break it up sufficiently to clean the catheter.

The service housings will generally be made of the same materials as are the housings for the implantable devices with which they are associated, such as titanium or stainless steel coated with a biocompatible elastomeric material, or entirely of a biocompatible plastic material. They will also usually be of a size less than about 150 cubic centimeters and of weight less than about 200 grams, although such size and weight is not critical.

While the sensors and catheters are shown connected to blood vessels, the sensors could be placed in any part of the body where monitoring of conditions is desired, such as in interstitial spaces or various organs, or the catheters could lead to various other body parts such as interstitial spaces or various organs.

Whereas this invention is here illustrated and described with specific reference to an embodiment thereof presently contemplated as the best mode of carrying out such invention in actual practice, it is to be understood that various changes may be made in adapting the invention to different embodiments without departing from the broader inventive concepts disclosed herein and comprehended by the claims that follow.

I claim:

1. In combination with a device adapted for at least partial implantation in a living body to perform a function with respect to such living body, and having a housing and a portion of such device extending from the housing through a hole therein into operative position in the body, such portion periodically needing servicing to maintain it in effective operating condition; positioning means for drawing said portion of the device that extends from the housing into the housing for periodic servicing and for reextending said portion into operating position in the body when servicing is complete; servicing means associated with said device and located within said housing for mechanically treating said device to enable it to maintain effective operation; and means for exercising control of said servicing means and said positioning means so as to periodically carry out a servicing function with respect to said device.

2. A combination according to claim 1, wherein the servicing means includes mechanical cleaning means.

3. A combination according to claim 2, wherein the mechanical cleaning means is a brush which is brought into contact with the surface of the device to be serviced.

4. A combination according to claim 3, wherein the mechanical cleaning means includes means for moving the brush against the surface to be serviced.

5. A combination according to claim 4, wherein the means for moving the brush rotates the brush about and against the surface to be serviced.

6. A combination according to claim 1, wherein the servicing means includes means for replacing a portion of the device to be serviced.

7. A combination according to claim 6, wherein the means for replacing a portion of the device includes means for removing the portion of the device to be replaced and for inserting a replacement therefor.

8. A combination according to claim 7, wherein the means for removing and replacing is a rotary tray having a plurality of stations and including means for rotating said tray, said tray being positioned so that when the device to be serviced is withdrawn into the housing, the portion thereof to be replaced is at a station, and upon rotation of the tray, the portion of the device to be replaced is removed from the device and a replacement portion is inserted in the device as the next station is positioned at the device.

9. A combination according to claim 1, wherein the means for exercising control of the servicing means includes a timing circuit to initiate servicing on a preset periodic basis.

10. A combination according to claim 1, wherein the means for exercising control of the servicing means includes means for receiving a signal from outside the body to initiate servicing.

11. A combination according to claim 1, wherein the means for exercising control of the servicing means includes means for monitoring the progress of the servicing and means for stopping servicing when servicing is completed.

12. A combination according to claim 1, wherein the means for exercising control of the servicing means includes means for monitoring operation of the device to be serviced to determine when servicing is necessary, and means for initiating servicing when servicing is necessary.

13. In combination with a device adapted for at least partial implantation in a living body to perform a function with respect to such living body and having as part of said device at least one catheter through which fluid flows during normal operation of the device and which needs periodic cleaning to maintain the catheter in open condition to allow the required flow of fluid therethrough, and means for causing normal operation of the device and normal flow of fluid through said catheter; servicing means in addition to the means for causing normal operation of the device associated with said device for maintaining the catheter in substantially open condition, said servicing means being at least partially located in a housing coupled to said catheter, and wherein a portion of the servicing means is extended from a position normally within the housing into the catheter for servicing of the catheter, and is withdrawn back into the housing after servicing; and means for exercising control of said servicing means so as to carry out the servicing function with respect to said catheter.

14. A combination according to claim 13, wherein the housing has an opening communicating with the device to be serviced and includes positioning means for extending the servicing means from the housing to proper servicing position and for withdrawing the servicing means into the housing when servicing is complete.

15. A combination according to claim 14, wherein the housing communicates with the catheter through a Y connection, wherein the servicing means is an obturator, and wherein the positioning means extends the obturator from the housing through the catheter to thereby clean the catheter and then withdraws it back into the housing.

16. A combination according to claim 14, wherein means are provided to block the ends of the catheter to be serviced when servicing is necessary, and wherein a servicing fluid is pumped from the housing into the catheter for servicing the catheter, and pumped back into the housing after servicing.

17. In combination with a device adapted for at least partial implantation in a living body to perform a function with respect to such living body and having as part of said device at least one catheter through which fluid flows during normal operation of the device and which needs periodic cleaning to maintain the catheter in open condition to allow the required flow of fluid therethrough, and means for causing normal operation of the device and normal flow of fluid through said catheter; servicing means in addition to the means for causing normal operation of the device associated with said device for maintaining the catheter in substantially open condition, said servicing means being at least partially located in a housing coupled to said catheter; and means for exercising control of said servicing means so as to carry out the servicing function with respect to said catheter, wherein a portion of the servicing means is permanently positioned with respect to the catheter and the remaining portion of the servicing means is located in the housing and causes operation of the portion of the servicing means permanently positioned when servicing is necessary, wherein the catheter includes a lumen, wherein the portion of the servicing means permanently positioned with respect to the catheter includes a flexible lumen wall, wherein the servicing means causes movement of the flexible lumen wall to thereby dislodge build-up of material in the lumen when servicing is desired, wherein the catheter has an outer wall and a flexible inner lumen wall, a closed compartment being formed between the outer and inner walls, and wherein the servicing means includes means for supplying a pressurized fluid to the compartment between the walls to thereby cause the flexible lumen wall to expand into the lumen when servicing is required to thereby break up and dislodge any catheter blockage.

18. A combination according to claim 17, wherein the means for supplying pressurized fluid includes a fluid reservoir and fluid pump in the service housing whereby fluid is pumped from the reservoir to the compartment between the catheter walls when servicing is required.

19. A combination according to claim 18, wherein the pump is a syringe type pump having a variable internal reservoir and having a combination inlet-outlet; wherein the housing includes a reservoir; wherein a passageway extends from the reservoir to the inlet-outlet of the pump; wherein a passageway extends from the inlet-outlet of the pump to the catheter to be serviced; wherein valves are provided in the passageway between the reservoir and the inlet-outlet of the pump and in the passageway between the catheter and the inlet-outlet of the pump so that with the valve to the catheter open and the valve to the reservoir closed, fluid may be pumped between the catheter and the internal reservoir of the pump, and with the valve to the catheter closed and the valve to the reservoir open, fluid can be pumped between the housing reservoir and the internal reservoir of the pump, but cannot flow into the catheter.

20. In combination with a device adapted for at least partial implantation in a living body to perform a function with respect to such living body and having as part of said device at least one catheter through which fluid flows during normal operation of the device and which needs periodic cleaning to maintain the catheter in open condition to allow the required flow of fluid therethrough, and means for causing normal operation of the device and normal flow of fluid through said catheter; servicing means in addition to the means for causing normal operation of the device associated with said device for maintaining the catheter in substantially open condition, said servicing means being at least partially located in a housing coupled to said catheter; and means for exercising control of said servicing means so as to carry out the servicing function with respect to said catheter, wherein a portion of the servicing means is permanently positioned with respect to the catheter and the remaining portion of the servicing means is located in the housing and causes operation of the portion of the servicing means permanently positioned when servicing is necessary, wherein the catheter includes a lumen, wherein the portion of the servicing means permanently positioned with respect to the catheter includes a flexible lumen wall, wherein the servicing means causes movement of the flexible lumen wall to thereby dislodge build-up of material in the lumen when servicing is desired, wherein pairs of electromagnets are embedded in opposite sides of the lumen wall and wherein the servicing means causes energization of the pairs of magnets to either attract or repel to thereby cause movement of the lumen wall.

21. In combination with a device adapted for at least partial implantation in a living body to perform a function with respect to such living body and having as part of said device at least one catheter through which fluid flows during normal operation of the device and which needs periodic cleaning to maintain the catheter in open condition to allow the required flow of fluid therethrough, and means for causing normal operation of the device and normal flow of fluid through said catheter; servicing means in addition to the means for causing normal operation of the device associated with said device for maintaining the catheter in substantially open condition, said servicing means being at least partially located in a housing coupled to said catheter; and means for exercising control of said servicing means so as to carry out the servicing function with respect to said catheter, wherein a portion of the servicing means is permanently positioned with respect to the catheter and the remaining portion of the servicing means is located in the housing and causes operation of the portion of the servicing means permanently positioned when servicing is necessary, wherein the catheter includes a lumen, wherein the portion of the servicing means permanently positioned with respect to the catheter includes a flexible lumen wall, and wherein the servicing means causes movement of the flexible lumen wall to thereby dislodge build-up of material in the lumen when servicing is desired, wherein electromagnets and pieces of magnetic material are associated as pairs and positioned in opposite sides of the lumen wall, and wherein the servicing means causes energization of the magnets to cause them to attract the magnetic material to thereby cause movement of the lumen wall.

22. In combination with a device adapted for at least partial implantation in a living body to perform a function with respect to such living body and having as part of said device at least one catheter through which fluid flows during normal operation of the device and which needs periodic cleaning to maintain the catheter in open condition to allow the required flow of fluid therethrough, and means for causing normal operation of the device and normal flow of fluid through said catheter; servicing means in addition to the means for causing normal operation of the device associated with said device for maintaining the catheter in substantially open condition, said servicing means being at least partially located in a housing coupled to said catheter; and means for exercising control of said servicing means so as to carry out the servicing function with respect to said catheter, wherein a portion of the servicing means is permanently positioned with respect to the catheter and the remaining portion of the servicing means is located in the housing and causes operation of the portion of the servicing means permanently positioned when servicing is necessary, wherein the catheter includes a lumen, wherein the portion of the servicing means permanently positioned with respect to the catheter is an expandable tube positioned in the lumen and wherein the servicing means includes means for supplying a pressurized fluid to the expandable tube to thereby cause it to expand into a lumen when servicing is required to thereby break up and dislodge any catheter blockage.

23. A combination according to claim 22, wherein the means for supplying pressurized fluid includes a fluid reservoir, and fluid pump in the service housing whereby fluid is pumped from the reservoir to the tube when servicing is required.

24. In combination with a device adapted for at least partial implantation in a living body to perform a function with respect to such living body and having as part of said device at least one catheter through which fluid flows during normal operation of the device and which needs periodic cleaning to maintain the catheter in open condition to allow the required flow of fluid therethrough, and means for causing normal operation of the device and normal flow of fluid through said catheter; servicing means in addition to the means for causing normal operation of the device associated with said device for maintaining the catheter in substantially open condition, said servicing means being at least partially located in a housing coupled to said catheter; and means for exercising control of said servicing means so as to carry out the servicing function with respect to said catheter, wherein a portion of the servicing means is permanently positioned with respect to the catheter and the remaining portion of the servicing means is located in the housing and causes operation of the portion of the servicing means permanently positioned when servicing is necessary, wherein the portion of the servicing means permanently positioned with respect to the catheter is a wire, and wherein the servicing means includes means for moving the wire within the catheter when servicing is desired.

25. In combination with a device adapted for at least partial implantation in a living body to perform a function with respect to such living body and having as part of said device at least one catheter through which fluid flows during normal operation of the device and which needs periodic cleaning to maintain the catheter in open condition to allow the required flow of fluid therethrough, and means for causing normal operation of the device and normal flow of fluid through said catheter; servicing means in addition to the means for causing normal operation of the device associated with said device for maintaining the catheter in substantially open condition, said servicing means being at least partially located in a housing coupled to said catheter; and means for exercising control of said servicing means so as to carry out the servicing function with respect to said catheter, wherein a portion of the servicing means is permanently positioned with respect to the catheter and the remaining portion of the servicing means is located in the housing and causes operation of the portion of the servicing means permanently positioned when servicing is necessary, wherein servicing of the catheter to be serviced includes heating at least a portion of the catheter, wherein a passageway for heated fluid is provided in the catheter about the portion to be heated, and wherein the servicing means causes the flow of heated fluid through such passageway.

26. In combination with a device adapted for at least partial implantation in a living body to perform a function with respect to such living body and having as part of said device at least one catheter through which fluid flows during normal operation of the device and which needs periodic cleaning to maintain the catheter in open condition to allow the required flow of fluid therethrough, and means for causing normal operation of the device and normal flow of fluid through said catheter; servicing means in addition to the means for causing normal operation of the device associated with said device for maintaining the catheter in substantially open condition, said servicing means being at least partially located in a housing coupled to said catheter; and means for exercising control of said servicing means so as to carry out the servicing function with respect to said catheter, wherein a portion of the servicing means is permanently positioned with respect to the catheter and the remaining portion of the servicing means is located in the housing and causes operation of the portion of the servicing means permanently positioned when servicing is necessary, wherein servicing of the catheter to be serviced includes heating at least a portion of the catheter, wherein a heating element is provided in the catheter about the portion to be heated, and wherein the servicing means causes energization of the heating element.

27. In combination with a device adapted for at least partial implantation in a living body to perform a function with respect to such living body and having as part of said device at least one catheter through which fluid flows during normal operation of the device and which needs periodic cleaning to maintain the catheter in open condition to allow the required flow of fluid therethrough, and means for causing normal operation of the device and normal flow of fluid through said catheter; servicing means in addition to the means for causing normal operation of the device associated with said device for maintaining the catheter in substantially open condition, said servicing means being at least partially located in a housing coupled to said catheter; and means for exercising control of said servicing means so as to carry out the servicing function with respect to said catheter, wherein a portion of the servicing means is permanently positioned with respect to the catheter and the remaining portion of the servicing means is located in the housing and causes operation of the portion of the servicing means permanently positioned when servicing is necessary, wherein electrode pairs are embedded in opposite sides of the catheter walls, and wherein the servicing means causes energization of the electrodes to create an electric field between them to cause electrophoresis to take place when servicing is necessary.

28. In combination with a device adapted for at least partial implantation in a living body to perform a function with respect to such living body and having as part of said device at least one catheter through which fluid flows during normal operation of the device and which needs periodic cleaning to maintain the catheter in open condition to allow the required flow of fluid therethrough, and means for causing normal operation of the device and normal flow of fluid through said catheter; servicing means in addition to the means for causing normal operation of the device associated with said device for maintaining the catheter in substantially open condition, said servicing means being at least partially located in a housing coupled to said catheter; and means for exercising control of said servicing means so as to carry out the servicing function with respect to said catheter, wherein the catheter and servicing means are connected by means of a passageway, and wherein the device is serviced by supplying a servicing fluid from the servicing means to the catheter, such servicing fluid being in addition to the fluid which flows through the catheter during normal operation of the device, wherein the servicing fluid is supplied to the catheter to flow into the body, wherein the servicing means includes means for moving a smaller catheter within the catheter to be serviced, and wherein means are provided to supply servicing fluid through said smaller catheter into the catheter to be serviced.

* * * * *

UNITED STATES PATENT AND TRADEMARK OFFICE
CERTIFICATE OF CORRECTION

PATENT NO. : 4,771,772
DATED : September 20, 1988
INVENTOR(S) : DeWitt James Lowell It is certified that error appears in the above-identified patent and that said Letters Patent is hereby corrected as shown below:

Title page, item [75],

The inventor's name should read --DeWitt James Lowell-- rather than "James L. DeWitt".

Column 6, line 60, change "deivce" to --device--.

Column 8, line 56, Change "losen" to --loosen--.

Column 12, line 7, change "in" to --is--.

Column 15, line 3, change "133" to --134--.

Signed and Sealed this

First Day of June, 1993

Attest:

MICHAEL K. KIRK

Attesting Officer

Acting Commissioner of Patents and Trademarks